US011291438B2

(12) United States Patent
 Ruppert

(10) Patent No.: US 11,291,438 B2
(45) Date of Patent: Apr. 5, 2022

(54) CLIP FOR BROAD SUTURE

(71) Applicant: Deep Blue Medical Advances, Inc., Durham, NC (US)

(72) Inventor: David Ruppert, Durham, NC (US)

(73) Assignee: Deep Blue Medical Advances, Inc., Durham, NC (US)

( * ) Notice: Subject to any disclaimer, the term of this patent is extended or adjusted under 35 U.S.C. 154(b) by 152 days.

(21) Appl. No.: 16/422,433

(22) Filed: May 24, 2019

(65) Prior Publication Data

US 2020/0367883 A1 Nov. 26, 2020

(51) Int. Cl.
*A61B 17/04* (2006.01)
*A61B 17/00* (2006.01)
*A61B 17/06* (2006.01)

(52) U.S. Cl.
CPC .... *A61B 17/0487* (2013.01); *A61B 17/06166* (2013.01); *A61B 2017/00004* (2013.01); *A61B 2017/0412* (2013.01)

(58) Field of Classification Search
CPC ........ A61B 17/0487; A61B 2017/0412; A61B 2017/00004; A61B 17/06166; A61B 2017/0456; A61B 2017/0464; A61B 2017/0404; A61B 2017/0417; A61B 17/0401; A61F 2/0063
See application file for complete search history.

(56) References Cited

U.S. PATENT DOCUMENTS

| | | | | | |
|---|---|---|---|---|---|
| 5,474,572 | A | * | 12/1995 | Hayhurst | A61B 17/0487 606/151 |
| 5,669,935 | A | * | 9/1997 | Rosenman | A61B 17/0487 606/232 |
| 5,810,853 | A | * | 9/1998 | Yoon | A61B 17/0487 606/151 |
| 5,895,393 | A | * | 4/1999 | Pagedas | A61B 17/0483 606/139 |
| 2005/0165424 | A1 | * | 7/2005 | Gallagher | A61B 17/0487 606/151 |

(Continued)

FOREIGN PATENT DOCUMENTS

| | | |
|---|---|---|
| JP | 2002515281 A | 5/2002 |
| KR | 101709041 B1 | 2/2017 |
| WO | 2018/031509 A1 | 2/2018 |

OTHER PUBLICATIONS

International Search Report and Written Opinion for International Application No. PCT/US2020/033771 dated Sep. 4, 2020.

*Primary Examiner* — Shaun L David
(74) *Attorney, Agent, or Firm* — Andrus Intellectual Property Law, LLP

(57) ABSTRACT

A clip includes a first side portion and a second side portion fastenable together and configured to attach to a broad suture. The first side portion has a first aperture sized to permit passage of the broad suture therethrough. The second side portion has a second aperture sized to permit passage of the broad suture therethrough, and at least one prong in the second aperture configured to penetrate the broad suture. A stopper surface is provided on the first side portion, wherein the prong contacts the stopper surface when the first side portion and the second side portion are fastened together so as to maintain the prong in the broad suture to thereby attach the clip to the broad suture.

23 Claims, 6 Drawing Sheets

(56) References Cited

U.S. PATENT DOCUMENTS

| | | |
|---|---|---|
| 2011/0313435 A1 | 12/2011 | Aldridge et al. |
| 2013/0226237 A1* | 8/2013 | Stanley .............. A61B 17/0401 606/232 |
| 2013/0268000 A1 | 10/2013 | Harner et al. |
| 2016/0270776 A1* | 9/2016 | Miraki ............... A61B 17/0487 |

* cited by examiner

CLIP FOR BROAD SUTURE

BACKGROUND

The present disclosure generally relates to implantable devices, and particularly to a clip attachable at the end of a broad suture, such as mesh suture, that has been sewn or woven into tissue.

Broad sutures, such as mesh sutures or tape sutures, are used to close high-tension wounds such as a hernia, and may be used for soft tissue to soft tissue fixation or soft tissue to bone fixation. A broad suture, or tape suture, is much wider than a typical thread suture, and the width offers many advantages. One continuing problem of these broad sutures is anchoring the suture in the flesh so that it does not pull out. While standard thread sutures are typically anchored with knots, knots are not as effective with broad sutures. Large knots are susceptible to increased palpability, pain, foreign body response, and may increase the risk of an infection. Thus, there is a need for an alternative anchoring device for broad sutures to prevent broad sutures from being pulled out or loosening once they have been implanted in tissue.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

In one embodiment, a clip includes a first side portion and a second side portion fastenable together and configured to attach to a broad suture. The first side portion has a first aperture sized to permit passage of the broad suture therethrough. The second side portion has a second aperture sized to permit passage of the broad suture therethrough, and at least one prong in the second aperture configured to penetrate the broad suture. A stopper surface is provided on the first side portion, wherein the prong contacts the stopper surface when the first side portion and the second side portion are fastened together so as to maintain the prong in the broad suture to thereby attach the clip thereto.

One embodiment of a clip for a broad suture includes a first side portion hingedly connected to a second side portion such that the first side portion and the second side portion are moveable with respect to one another to open and close the clip. The first side portion has a first aperture sized to permit passage of the broad suture therethrough. The second side portion has a second aperture sized to permit passage of the broad suture therethrough. The clip is configured such that the broad suture can pass through the first aperture and the second aperture when the clip is open so that the clip can be slid down a length of the broad suture. At least one prong is provided that engages the broad suture when the clip is closed so that the clip attaches to the broad suture.

Various other features, objects, and advantages of the invention will be made apparent from the following description taken together with the drawings.

BRIEF DESCRIPTION OF THE DRAWINGS

The present disclosure is described with reference to the following Figures.

DETAILED DESCRIPTION

Figure 1:
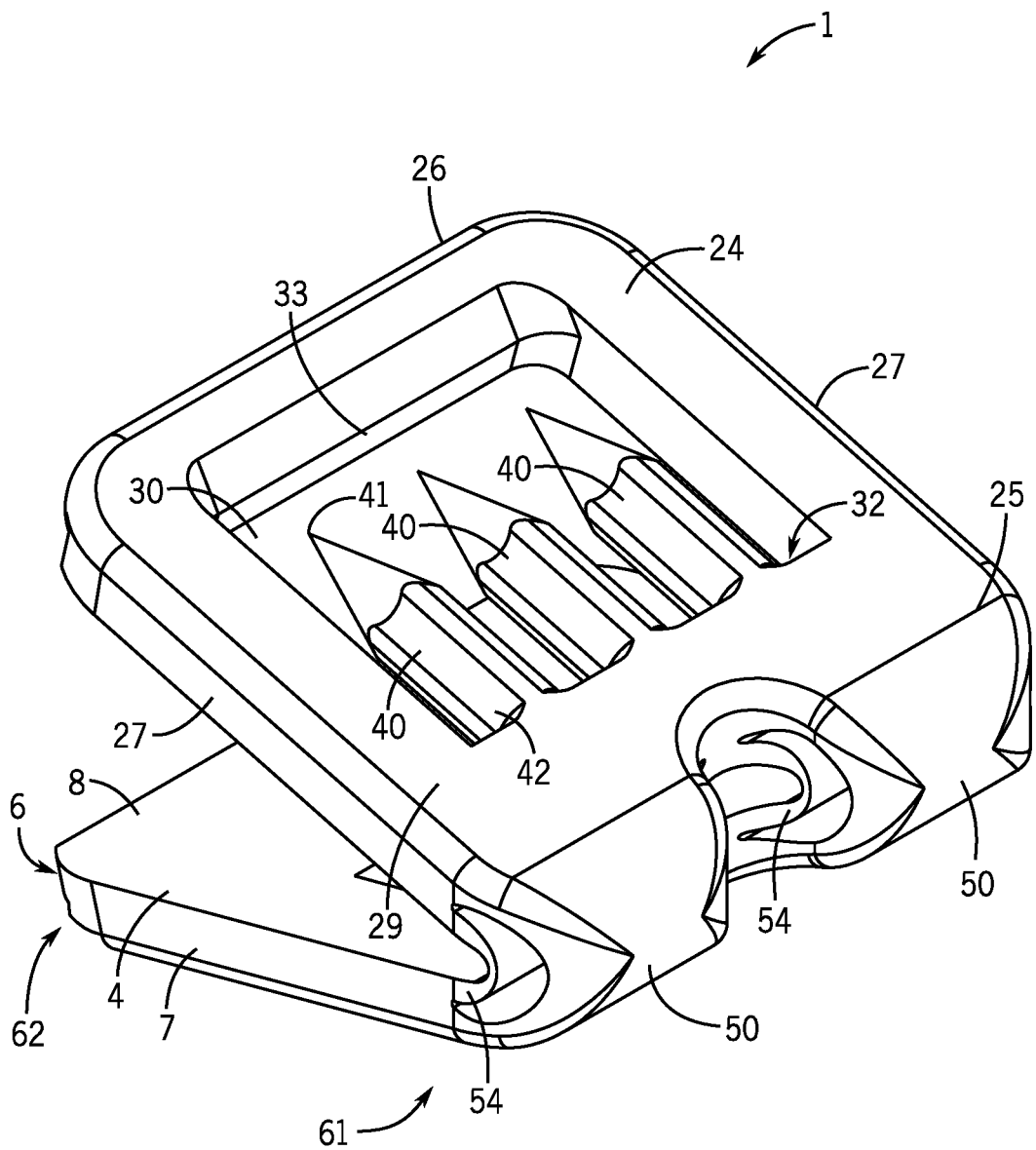
FIG. 1 is a perspective view of an embodiment of a clip for a broad suture when the clip is open.

The inventors have recognized a need for an improved method of anchoring broad sutures, or wide sutures, implanted in tissue. Various forms of broad sutures are used for soft tissue repair and for fixation applications, including mesh sutures, mesh extensions, suture tape (e.g. textile suture tape, allograft or xenograft tape, polymer tape, or a composite tape), and tape extensions. As disclosed herein, the present inventors have developed a clip for a broad suture that is slideable down a length of the broad suture and closeable to attach the clip to the broad suture. The attached clip acts as a washer against the tissue to prevent the broad suture from being pulled back through the tissue. The clip includes two side portions fastenable together to attach to a broad suture. Each side portion has an aperture through which the broad suture can be passed. The clip is configured such that when it is open, the broad suture can pass through the apertures of both side portions and when the clip is closed it attaches to the broad suture.

FIGS. 1-4 depict one embodiment of a clip 1 from various view angles and in various open and closed positions. In the embodiment, a first side portion 4 and a second side portion 24 are openable and closeable with respect to one another. In the depicted embodiment, the first side portion 4 and the second side portion 24 are hingedly connected at one end such that they open and close with respect to one another. The first side portion 4 has a first aperture 10 sized to permit passage of a broad suture 85 therethrough (see also FIGS. 5A-5B). The second side portion 24 also has an aperture 30 (referred to herein as the second aperture 30) also sized to permit passage of the broad suture 85 therethrough.

The second side portion 24 is configured with one or more prongs 40 configured to penetrate the broad suture, such as to puncture the broad suture or penetrate the pores of the mesh suture being passed therethrough in order to engage the broad suture. The prongs 40 extend into the second aperture 30 and are arranged such that the broad suture is permitted to pass through the aperture 30 such that it can be slid down an implanted broad suture, starting at a distal end and traveling toward the implantation site where the broad suture has been woven or sewn into tissue. When the clip 1 is open, it can be freely slid down the broad suture into a blind region of the body without engaging the broad suture material, such as the mesh pores, due to the angle at which the broad suture is directed through the first and second apertures 10 and 30 and the position of the prongs 40 with respect thereto. Namely, the prongs 40 are oriented such that the mesh pores, for example, do not catch on the prongs 40 as the clip 1 is being slid down the broad suture.

Figure 2:
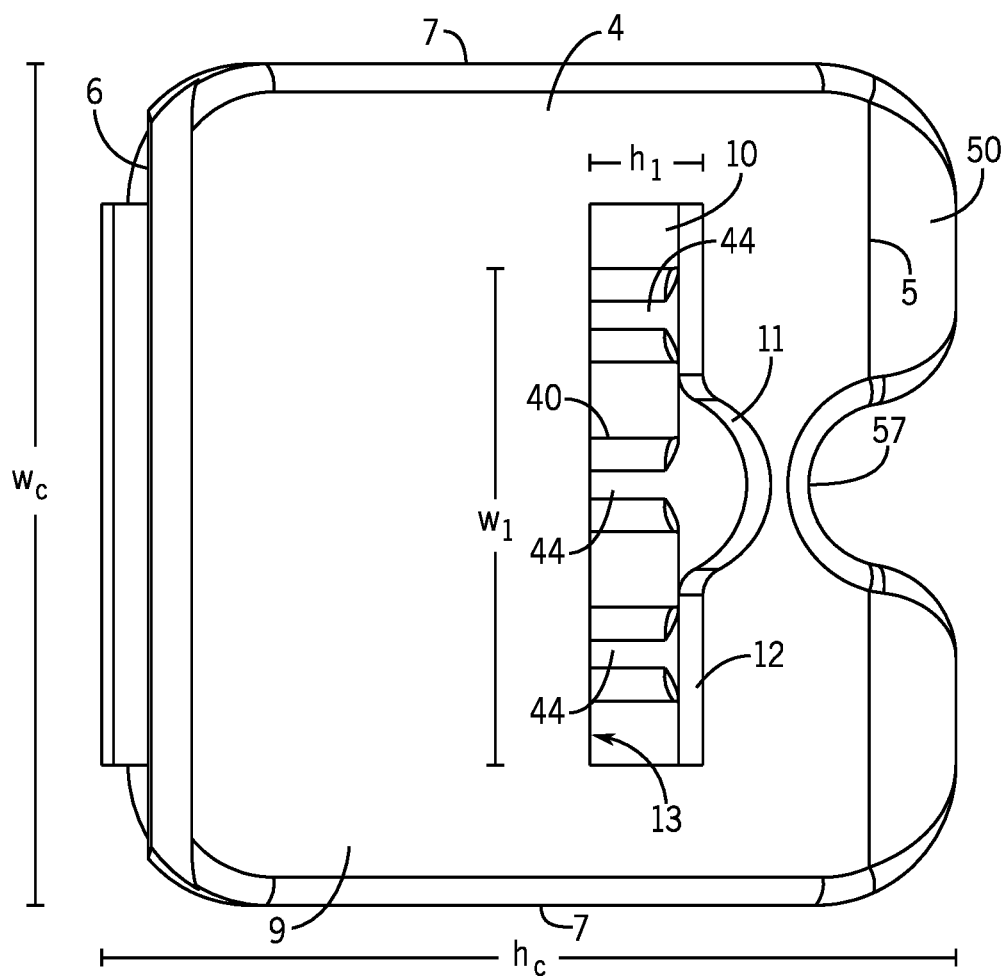
FIG. 2 is a view of the first side of the embodiment of the clip when the clip is closed.
Figure 3:
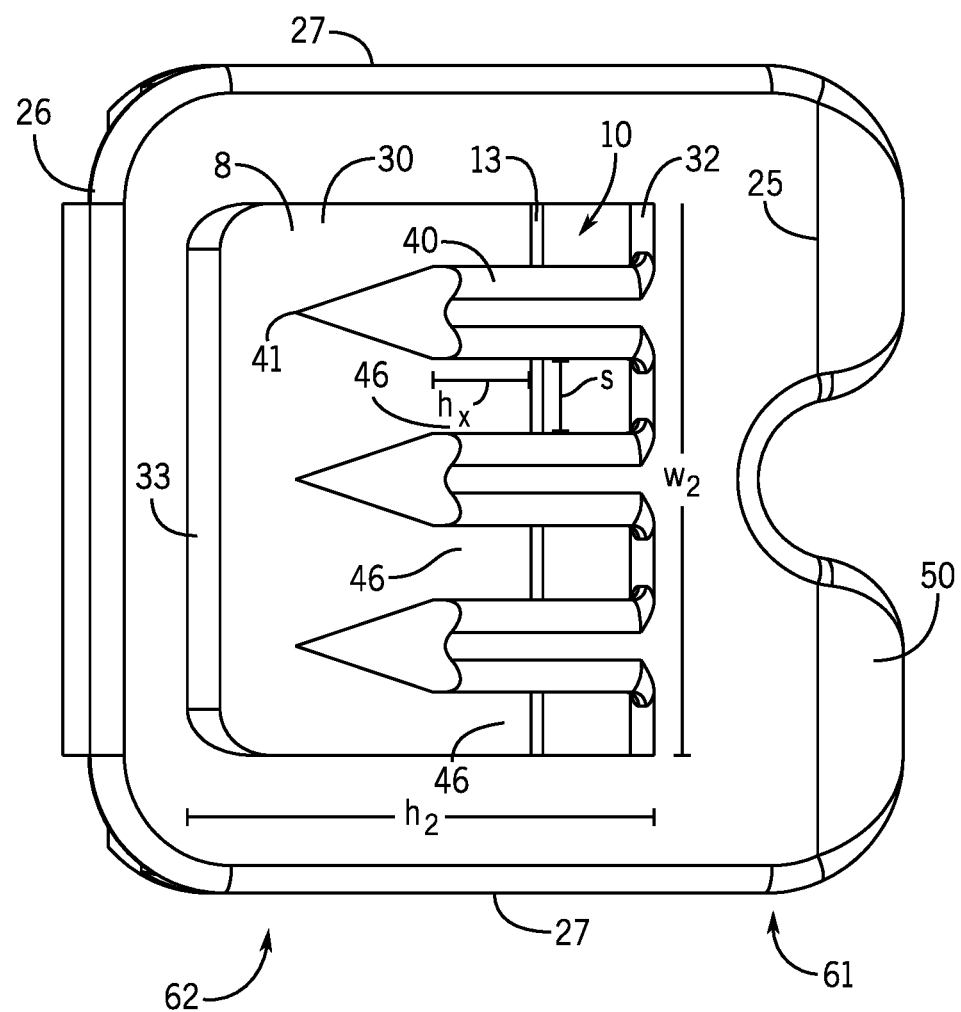
FIG. 3 is a view of the second side of the embodiment of the clip when the clip is closed.

When the clip 1 is closed such that the first and second portions 4 and 24 are pressed together, the prongs 40 are forced into and through the broad suture, such as through the pores of the mesh, and act to anchor the clip 1 onto the suture. As shown in FIGS. 2 and 3, the prongs 40 contact a stopper surface 46 on the opposing first side portion 4. Thus, the suture is not permitted to slide off of the prongs 40 and the clip is held in place on the broad suture 85 (see also FIG. 6). Namely, the one or more prongs 40 in the second aperture 30 engage the suture and contact the stopper surface 46 with sufficient force to maintain engagement with the broad suture material so that the clip 1 is held in place on the broad suture 85 and can act as a washer against the tissue 90 to prevent the broad suture from pulling out of the tissue once the tissue is placed under load (such as load caused by a patient's normal healthy activity).

Figure 6:
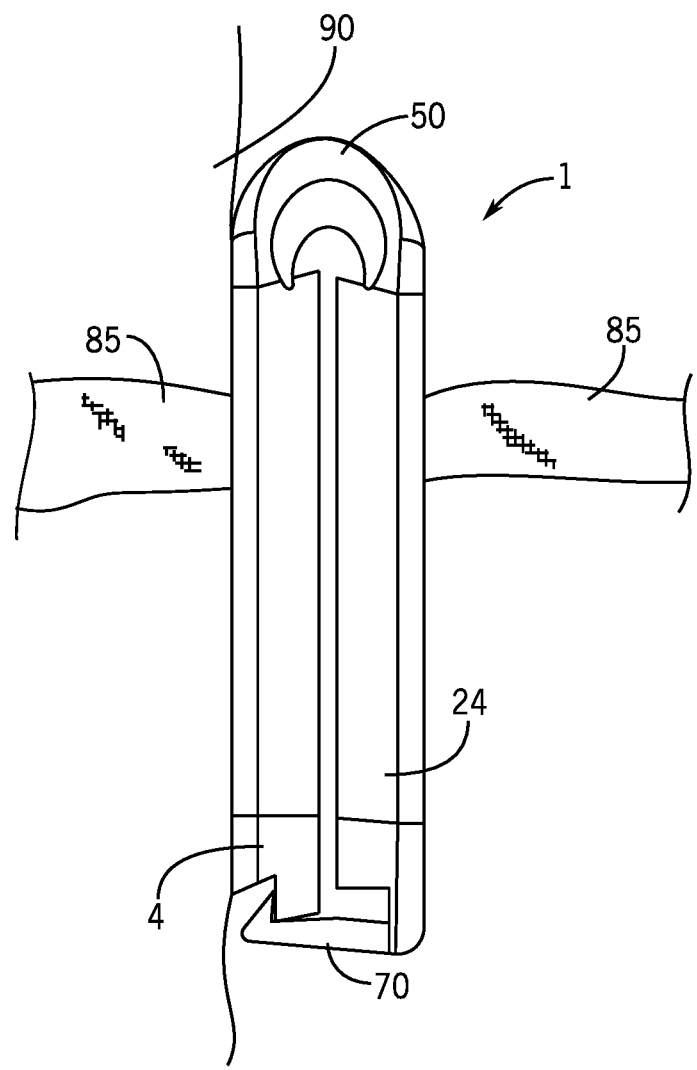
FIG. 6 depicts one embodiment of a clip attached to a broad suture implanted in tissue.

The clip 1 is sufficiently large to prevent it from passing through the hole created by pulling the broad suture 85 through the fascia. Meanwhile, the thickness $d_c$, or depth (FIG. 4), of the clip and the overall size of the clip is sufficiently minimized so as to limit risks of foreign body response and infection risk and minimizing palpability and pain. Where the clip 1 is comprised of a degradable, biocompatible material, minimizing the thickness and overall size of the clip 1 also encourages appropriate bioincorporation. In other embodiments the clip 1 may be permanent (non-degradable). Referring also to FIG. 6, the surface area of the clip 1 normal to the direction of the broad suture 85 is sufficiently large enough to prevent the device from being pulled through the hole created by passing the broad suture 85 through the fascia 90.

The size of the clip 1 may vary depending on the size of the broad suture 85. The clip 1 has a height $h_c$ and a width $w_c$. Preferably, the clip has a width $w_c$ that is wider than the broad suture such that the suture can be relatively flat when it passes through the apertures 10, 30 of the clip 1. Accordingly, the apertures 10, 30 may have a width $w_1$ that is at least as wide as the width $w_s$ of the suture. In one embodiment, the surface area normal to the direction of the broad suture 85 is at least 25 mm$^2$ or larger, in another embodiment the surface area is at least 50 mm$^2$ or larger, in another embodiment the surface area is at least 100 mm$^2$ or larger.

Referring to FIGS. 1-3, each of the first side portion 4 and the second side portion 24 have an inside face 8, 28 and an outside face 9, 29. The inside faces 8, 28 contact one another when the clip 1 is closed. The outside faces 9, 29 form the outer faces of the clip 1. Each side portion 4, 24 has a bottom edge 5, 25 and a top edge 6, 26. In the depicted example, the side portions 4, 24 are hingedly connected at their respective bottom edges 5, 25, which is on the bottom side 61 of the clip 1. The clip 1 has a clasp or fastening mechanism at the top side 62 that holds the clip 1 closed, fastening the top edges 6 and 26 together. Opposing side edges 7, 27 connect the respective top edges 6, 26 and bottom edges 5, 25. In other embodiments, the fastening mechanism may be provided on one or more of the side edges 7, 27, or elsewhere on the clip 1.

Figure 5A:
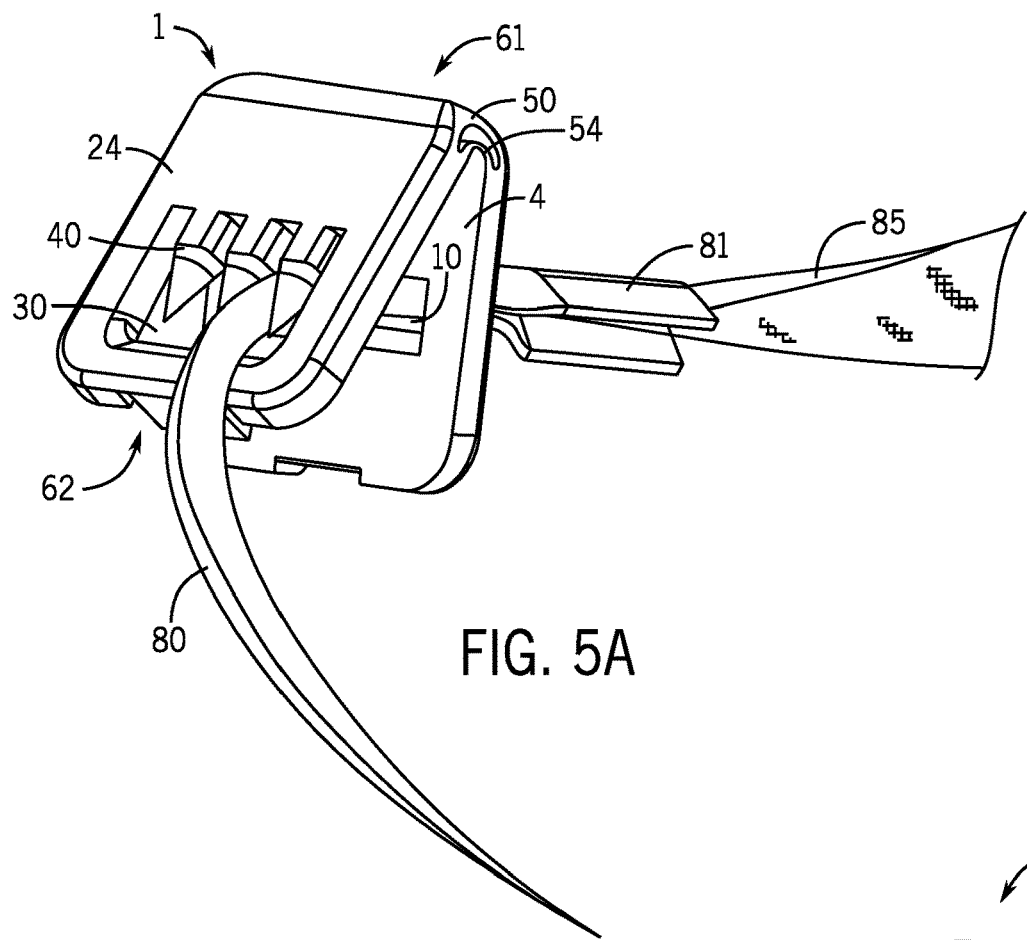
FIGS. 5A and 5B depict another embodiment of a clip for a broad suture showing a surgical needle being inserted therethrough.
Figure 5B:
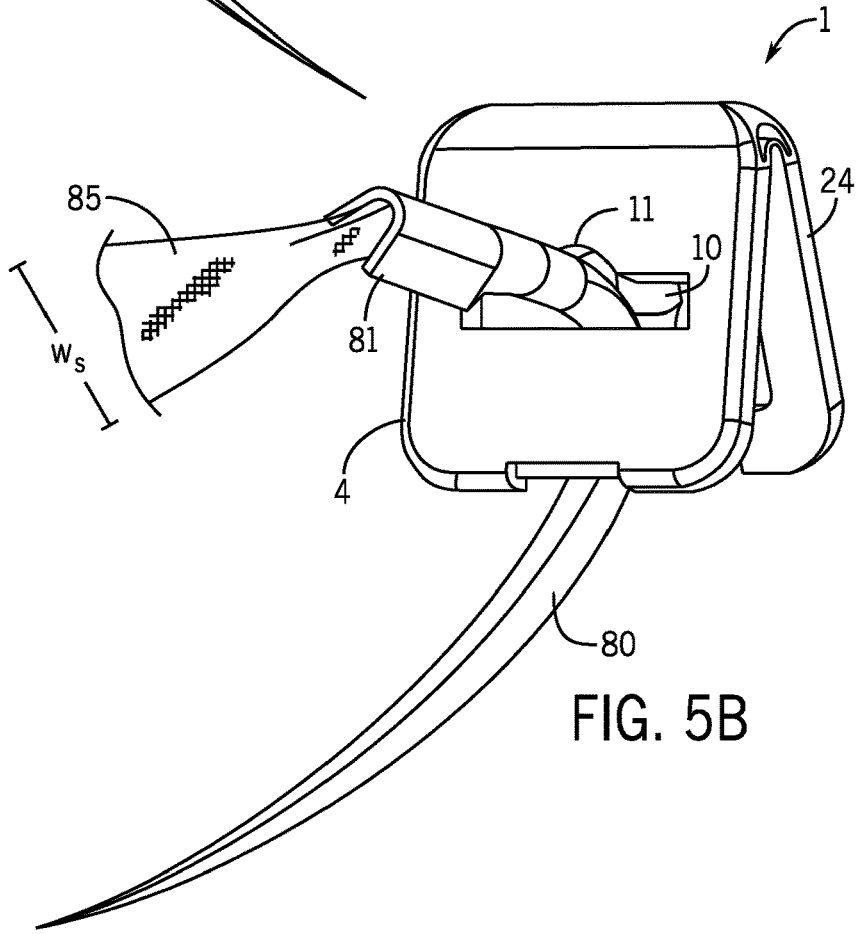

The first side portion has an aperture 10 configured to permit a broad suture 85 to pass through the first side portion 4. Accordingly, the aperture 10 has a width $w_1$ and a height $h_1$ that are large enough such that a broad suture can pass relatively easily therethrough. In one embodiment, the width $w_1$ is sized larger than a width $w_s$ of the suture (see FIG. 5B). The height $h_1$ is sufficient such that the broad suture can easily pass through the aperture 10 at an appropriate angle as the clip 1 is slid down the broad suture 85. The aperture 10 has a lower edge 12 and an upper edge 13. At least one of the lower edge 12 and the upper edge 13 may have a notch 11 configured to allow passage of a suture needle 80 to which the broad suture 85 is attached. As illustrated in FIGS. 5A and 5B, the needle 80 is fed through the apertures 10, 30. The broad suture 85 is attached to the connection end 81 at the back end of the needle 80 such that the broad suture 85 can be pulled through the apertures 10 and 30.

The second aperture has a width $w_2$ and a height $h_2$. The second aperture 30 may have a width $w_2$ that is equal to, or approximately equal to, the width $w_1$ of the first aperture 10. However, the height $h_2$ of the second aperture 30 is greater than the height $h_1$ of the first aperture 10. The aperture 30 in the second side portion 24 includes at least one prong 40 and the height $h_2$ is sufficient that the broad suture 85 can pass between a tip 41 of the prong 40 and the upper edge 33 of the aperture 30.

In the depicted embodiments, the aperture 30 in the second side portion 24 is larger than the aperture 10 in the first side portion 4. The aperture 30 has a lower edge 32 and an upper edge 33. In the depicted embodiments, the lower edge 32 of the second aperture 30 aligns with the lower edge 12 of the first aperture 10. The first aperture 10 is configured with a smaller height $h_1$ such that the broad suture 85 passing therethrough contacts the upper edge 13 of the first aperture 10 and angles upward to the upper portion of the second aperture 30 so as to pass above the prongs 40. In certain embodiments, the upper edge 13 of the first aperture 10 may be sloped, or ramped, at an angle to facilitate passage of the broad suture 85 at an upward-angle toward the upper edge 33 of the second aperture 30 (see FIG. 3).

At least one prong 40 extends into the second aperture 30. The prong 40 is configured to penetrate the broad suture, such as to pass through the mesh pores, in order to fix the clip 1 to the broad suture 85. Accordingly, the prong 40 has a diameter that is less than the maximum diameter of the broad suture pore. In the depicted embodiment, the clip 1 has three prongs 40 each having approximately equal height and terminating at a tip 41. The prongs 40 have a pointed, or conical, top end terminating at tip 41. This shape may facilitate passage of the suture through the clip 1 in the direction where the suture passes along the tapered top edge so that the clip can slide down the broad suture 85. However, the clip 1 will not easily slide backward up the broad suture 85 because the tips 41 of the prongs 40 may grab and penetrate the pores of the suture. In the depicted example, the prongs 40 have a conical-shaped base 42 that extends from the lower edge 32 of the second aperture 30. In other embodiments, the prongs 40 may be differently shaped, such as conical with a rounded tip or flat tip, or may be rectangular in shape.

The clip 1 includes at least one prong 40. The depicted embodiment includes three prongs 40; however, in other embodiments the clip may have two prongs 40, or may have more than three prongs 40. The prongs 40 are positioned to penetrate sufficiently distant portions of the broad suture, such as different pores of the mesh, so as to attach to the suture without ripping it or overly weakening the material. In certain embodiments, the prongs 40 are sufficiently spaced apart such that they penetrate nonadjacent pores. In the depicted example, the prongs 40 are spaced apart by a distance s. In certain examples, the distance s between the prongs may be between 5% and 20% of $w_2$. To provide just one example, in one embodiment $w_2$ is 6 mm and distance s is 0.831 mm.

The prongs 40 are configured such that they contact a stopper surface 46 when the clip 1 is closed, which is an opposing surface on the first side portion 4. As best seen in FIG. 2, the prongs 40 have an inside surface 44 that contacts the stopper surface 46. The contact between the inside surface 44 of the prong 40 and the stopper surface 46 of the first side portion 4 holds the suture in place and maintains the prong 40 in the suture. Thereby, the clip 1 is kept in place and attached to the broad suture. In other words, the frictional engagement between the stopper surface 46 and the inside surface 44 of the prong prevents the suture from sliding between those surfaces and thus holds the clip in place on the broad suture 85. In the depicted embodiment, the prongs 40 are coplanar with the second side portion 24. The prongs 40 may have the same depth as that of the second side portion 24. In one preferred embodiment, the inside surface 44 of the prongs 40 is coplanar with the inside face 28 of the second side portion 24 such that the inside surface 44 contacts the stopper surface 46, which is flush with the inside face 8 of the first side portion 4. In other embodiments, the stopper surface 46 may protrude from the inside face 8 so as to enable contact with the prong 40. The height $h_x$ of the contact surface is sufficient to prevent the broad suture 85 from moving off of the prong 40.

Figure 4:
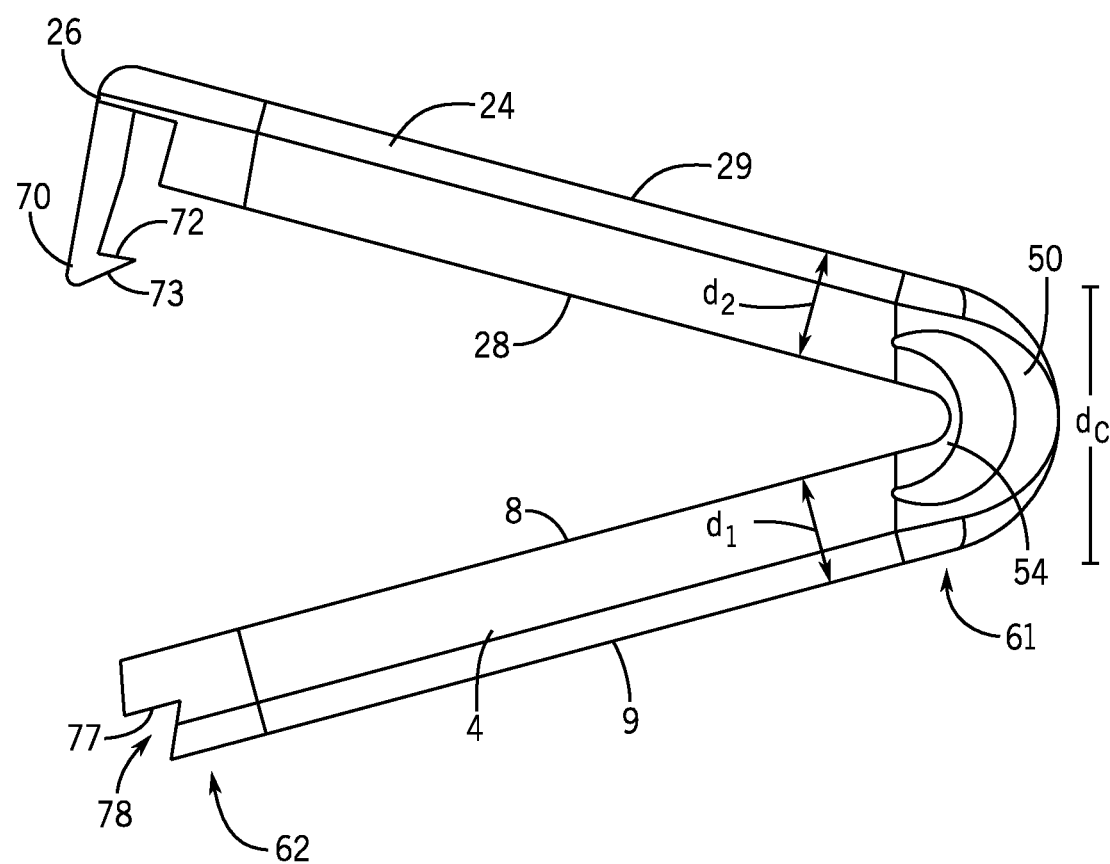
FIG. 4 is a side view of the embodiment of the clip when the clip is open.

Referring to FIG. 4, the clip has a total depth $d_c$. When the clip is in the closed position, the depth $d_c$ of the clip is comprised of the depth $d_1$ of the first side portion 4 and the depth $d_2$ of the second side portion 24. In one exemplary embodiment, the depth $d_c$ of the clip is between 0.25 and 10 mm, and more commonly may be between 1 and 3 mm. The depths $d_1$ and $d_2$ of the respective side portions 4 and 24 may be equal to one another, and thus equal to half of the depth $d_c$ of the closed clip 1. In other embodiments, the depth $d_1$ and $d_2$ of the respective side portions 4, 24 may be different from one another. For example, the depth $d_2$ of the second side portion may be greater than the depth $d_1$ of the first side portion.

The first side portion 4 and the second side portion 24 may be hingedly connected, as described above. FIG. 4 depicts one embodiment of a hinge arrangement for the bottom side 61 of the clip 1. The hinge arrangement includes a main hinge 50 connecting the bottom edges 5, 25 of the respective side portions 4, 24. In the depicted embodiment, the hinge 50 is a living hinge, which is a thin, flexure-bearing portion made from the same material as the two side portions 4, 24. The clip 1 is configured to bend at the hinge 50, and thus is comprised of a material that permits flexure at the hinge portion. In other embodiments, the hinge 50 may be a separate element that is attached to the first side portion 4 and the second side portion 24, such as a butt hinge, a piano hinge, a flush hinge, or the like.

In the embodiment of FIG. 4, a second inner hinge 54 is also included and connects the first and second side portions 4, 24. In the depicted example, the inner hinge 54 is also a living hinge and is configured to bias the clip 1 toward the open position. The inner hinge 54 may be a sacrificial hinge that breaks when the clip 1 is fully closed. Thereby, the inner hinge 54 is configured to allow a biasing force to hold the first and second side portions 4, 24 in an open position as the clip 1 is slid down the broad suture. Then, once the clip is positioned, it can be fully closed in order to break the inner hinge 54 to eliminate the biasing force. Once the inner hinge 54 is broken, the clip will stay in the closed position unless forced open. In other embodiments, the inner hinge 54 may be a separate device connected to the side portions 4, 24, such as a spring hinge configured to bias the clip open. In one embodiment, the inner and outer hinges 54, 50 may be replaced by a single hinge, such as a spring hinge or hinge configured to bias the clip 1 toward the open position. In embodiments where the clip 1 is biased open, a fastening mechanism is provided to maintain the clip in a closed position once in place on the broad suture.

As shown in FIGS. 1-3, the hinge 50 and/or the hinge 54 may be comprised of two side portions. Specifically, a notch 57 may be formed in the bottom edge, thereby providing two hinges, one positioned on either side of the bottom side 61 of the clip 1. The split hinge arrangement may facilitate certain functionality, such as permitting better manufacturing control of the living hinges. Additionally, the split hinge arrangement may provide better and more consistent breakage for the sacrificial hinge and also allow the main hinge 50 to be more easily broken for purposes of removing an installed clip 1 from an implanted broad suture 85. In other embodiments, the hinge 50 may be a single element that extends all or most of the way across the bottom side 61 of the clip 1, such as shown in FIGS. 5A and 5B.

The clip 1 may include a clasp or other fastening device that holds the side portions 4, 24 together to maintain the clip 1 in the closed position. FIG. 4 depicts one embodiment of a clasp 70 configured to fasten the side portions 4, 24 together, and in the depicted arrangement is positioned on the top side 62 of the clip. The depicted arrangement is a hook-type clasp arrangement where the hook-clasp 70 is located on the top edge 26 of the second side portion 24. When the clip 1 is closed, the hook 72 engages an engagement edge 77 on a top edge 6 of the first side portion 4. In the depicted example, the clasp 70 has a ramped edge 73 that causes the clasp 70 to flex outward as it slides against the top edge 6 of the first side portion 4 during closure. Once the hook 72 reaches the recessed portion 78 on the top edge 6, the clasp 70 is forced closed and the hook portion 72 engages the engagement edge 77 to maintain the clip 1 closed. In order to open the clip 1, the clasp 70 can be manually forced outward by a user such that the hook 72 clears the engagement edge 77 and permits opening of the clip 1. In various other embodiments, other fastening arrangements may be employed, and many types of fasteners are well known in the art of medical implants.

The hinge may be comprised of various biocompatible materials, such as biocompatible metal or plastic material. In one embodiment, the clip 1 is formed as a single molded piece, such as be injection molded. Alternatively, the clip 1 may be manufactured by 3D printing. In one embodiment, the clip 1 is comprised of PolyEtherEtherKetone (PEEK), polylactic acid (PLA), or another biocompatible polymer or copolymer. In certain embodiments, the clip 1 is made of a biodegradable polymer that can be injection molded, such as injection molded polylactic acid (PLA) or polylactic-co-glycolic acid (PLGA). Alternatively, the clip 1 is fabricated in either a permanent metal (e.g. titanium) or a degradable metal (e.g. magnesium).

This written description uses examples to disclose the invention, including the best mode, and also to enable any person skilled in the art to make and use the invention. Certain terms have been used for brevity, clarity and understanding. No unnecessary limitations are to be inferred therefrom beyond the requirement of the prior art because such terms are used for descriptive purposes only and are intended to be broadly construed. The patentable scope of the invention is defined by the claims, and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

I claim:
1. A clip for a broad suture, the clip comprising:
 a first side portion and a second side portion that are fastenable together to attach to a broad suture;

the first side portion having a first depth and a first aperture through the first depth sized to permit passage of the broad suture through the first side portion;

the second side portion having a second depth and a second aperture through the second depth sized to permit passage of the broad suture through the second side portion and at least one prong in the second aperture, wherein the prong is configured to penetrate the broad suture; and a stopper surface on the first side portion;

wherein the prong and the stopper surface are configured such that the prong contacts the stopper surface when the first side portion and the second side portion are fastened together so as to maintain the prong in the broad suture and attach the clip to the broad suture.

2. The clip of claim 1, wherein the clip is configured such that when the first side portion and the second side portion are in an open position with respect to one another, the broad suture can slide through the first aperture and the second aperture such that the clip is slidable down a length of the broad suture.

3. The clip of claim 2, wherein the prong extends from a lower edge of the second aperture and toward an upper edge of the second aperture, wherein the broad suture passes between a tip of the prong and the upper edge of the second aperture.

4. The clip of claim 3, wherein the first aperture is located closer to a bottom end of the clip than a top end of the clip.

5. The clip of claim 4, wherein the prong is co-planar with the second side portion.

6. The clip of claim 1, wherein the first side portion has an inner side that contacts an inner side of the second side portion when the side portions are attached, and wherein the stopper surface is on the inner side of the first side portion.

7. The clip of claim 1, wherein the clip is configured such that when the first side portion and the second side portion are fastened together on the broad suture, the clip sits substantially perpendicularly to a length of the broad suture.

8. The clip of claim 1, wherein, when attached to the broad suture, the clip is configured to acts as a washer against tissue in which the broad suture is sewn.

9. The clip of claim 1, wherein the first aperture has a notch on at least one of an upper edge and a lower edge configured to permit passage of a suture needle therethrough.

10. The clip of claim 1, wherein the first side portion and the second side portion are hingedly connected.

11. The clip of claim 1, wherein the first side portion and the second side portion are attached at a bottom edge by a hinge.

12. The clip of claim 11, further comprising a clasp extending from one of the first side portion and the second side portion, wherein the clasp is configured to engage an engagement edge of the other one of the first side portion and the second side portion.

13. The clip of claim 1, wherein the clip is a single molded piece of degradable biocompatible material.

14. The clip of claim 1, wherein the clip is a single molded piece of non-degradable biocompatible material.

15. A clip for a broad suture, the clip comprising:

a first side portion hingedly connected to a second side portion such that the first side portion and the second side portion are movable with respect to one another to open and close the clip;

the first side portion having a first depth and a first aperture through the first depth sized to permit passage of the broad suture through the first side portion;

the second side portion having a second depth and a second aperture through the second depth sized to permit passage of the broad suture through the second side portion;

wherein the clip is configured such that the broad suture can pass through the first aperture and the second aperture when the clip is open so that the clip is slidable down a length of the broad suture; and at least one prong that engages the broad suture when the clip is closed such that the clip attaches to the broad suture.

16. The clip of claim 15, wherein the prong extends from a lower edge of the second aperture and is configured to contact a stopper surface on the first side portion when the clip is closed so as to maintain the prong engaged in the broad suture.

17. The clip of claim 16, wherein the prong is co-planar with the second side portion.

18. The clip of claim 15, further comprising a hinge connecting a bottom edge of the first side portion and a bottom edge of the second side portion.

19. The clip of claim 18, wherein the hinge is a living hinge.

20. The clip of claim 15, further comprising an inner hinge configured to bias the clip open.

21. The clip of claim 20, wherein the inner hinge is a sacrificial hinge that breaks when the clip is closed.

22. The clip of claim 15, further comprising a clasp extending from one of the first side portion and the second side portion, wherein the clasp is configured to engage an engagement edge of the other one of the first side portion and the second side portion.

23. The clip of claim 15, wherein the clip is formed of injection molded polylactic acid (PLA) or polylactic-co-glycolic acid (PLGA).

* * * * *